(12) United States Patent
Duan

(10) Patent No.: US 9,656,233 B2
(45) Date of Patent: May 23, 2017

(54) REVERSIBLE MICROCAPSULE FILTER CAKE

(71) Applicant: Biao Duan, Appleton, WI (US)

(72) Inventor: Biao Duan, Appleton, WI (US)

(73) Assignee: Encapsys, LLC, Appleton, WI (US)

( * ) Notice: Subject to any disclaimer, the term of this patent is extended or adjusted under 35 U.S.C. 154(b) by 127 days.

(21) Appl. No.: 14/599,014

(22) Filed: Jan. 16, 2015

(65) Prior Publication Data
US 2016/0207020 A1    Jul. 21, 2016

(51) Int. Cl.
*B01J 13/02* (2006.01)
*A61K 9/50* (2006.01)
(Continued)

(52) U.S. Cl.
CPC .......... *B01J 13/046* (2013.01); *A61K 9/5089* (2013.01); *B01D 37/03* (2013.01); *B01J 13/02* (2013.01); *B01J 13/025* (2013.01); *B01J 13/04* (2013.01); *B01J 13/20* (2013.01); *C02F 1/5236* (2013.01); *C02F 1/542* (2013.01); *C02F 1/66* (2013.01); *C02F 11/121* (2013.01); *C02F 11/127* (2013.01); *C02F 11/14* (2013.01); *A61K 9/50* (2013.01); *A61K 49/0091* (2013.01); *A61K 49/18* (2013.01); *A61K 51/12* (2013.01); *C02F 1/68* (2013.01); *C02F 2209/06* (2013.01); *C08J 3/00* (2013.01); *C08J 3/05* (2013.01); *C08J 2333/00* (2013.01)

(58) Field of Classification Search
None
See application file for complete search history.

(56) References Cited

U.S. PATENT DOCUMENTS

| | | | |
|---|---|---|---|
| 3,494,872 A | * | 2/1970 | Maierson ................. B01J 13/10 264/4.4 |
| 4,499,236 A | | 2/1985 | Hermann et al. |

(Continued)

FOREIGN PATENT DOCUMENTS

| | | |
|---|---|---|
| EP | 0152083 A2 | 8/1985 |
| EP | 2106704 B1 | 12/2013 |
| GB | 1139964 | 1/1969 |

OTHER PUBLICATIONS

International Search Report for PCT/US2016/03148.

*Primary Examiner* — Clare Perrin
(74) *Attorney, Agent, or Firm* — Benjamin Mieliulis

(57) ABSTRACT

The invention teaches a method of efficiently dewatering a microcapsule slurry to form a water re-suspendable filter cake of microcapsules. The process comprises providing an aqueous slurry of microcapsules dispersed in an aqueous solution; adding an agglomeration agent and dispersing the agglomeration agent into the aqueous slurry; adjusting the pH to a pH level sufficient to agglomerate the dispersed microcapsules; and filtering the aqueous slurry of microcapsules by gravity, vacuum or pressure filtration to thereby form a filter cake of dewatered microcapsules. The agglomeration agent is sodium polyphosphate, sodium tetrapolyphosphate, sodium hexametaphosphate, and/or sodium tripolyphosphate; or with anionic microcapsules or coatings even alkaline earth metal salts such as magnesium chloride, calcium chloride or barium chloride, or even aluminum salt such as aluminum chloride.

10 Claims, 2 Drawing Sheets

(51) Int. Cl.
  *B01J 13/04* (2006.01)
  *B01D 21/01* (2006.01)
  *C02F 1/52* (2006.01)
  *B01J 13/20* (2006.01)
  *C02F 1/54* (2006.01)
  *C02F 11/12* (2006.01)
  *C02F 1/66* (2006.01)
  *C02F 11/14* (2006.01)
  *B01D 37/03* (2006.01)
  *B32B 5/16* (2006.01)
  *B32B 27/00* (2006.01)
  *B32B 27/34* (2006.01)
  *B32B 27/30* (2006.01)
  *B01J 13/00* (2006.01)
  *B01D 21/00* (2006.01)
  *C02F 1/00* (2006.01)
  *B03D 3/00* (2006.01)
  *B01D 37/00* (2006.01)
  *A61K 49/18* (2006.01)
  *A61K 51/12* (2006.01)
  *A61K 49/00* (2006.01)
  *C02F 1/68* (2006.01)
  *C08J 3/00* (2006.01)
  *C08J 3/05* (2006.01)

(56) References Cited

U.S. PATENT DOCUMENTS

| | | | |
|---|---|---|---|
| 4,601,863 A * | 7/1986 | Shioi | B41M 5/165 252/299.7 |
| 5,030,286 A | 7/1991 | Crawford et al. | |
| 5,069,831 A * | 12/1991 | Schwab | G03F 7/002 264/4.3 |
| 5,196,149 A * | 3/1993 | Scarpelli | B01J 13/10 106/31.24 |
| 7,122,080 B2 | 10/2006 | Pruett et al. | |
| 7,303,794 B2 | 12/2007 | Superka et al. | |
| 8,152,931 B2 | 4/2012 | Tropsch | |
| 8,747,999 B2 * | 6/2014 | Grey | B01J 13/02 428/402 |
| 2005/0164116 A1 * | 7/2005 | Wang | B01J 13/18 430/138 |
| 2006/0006560 A1 | 1/2006 | Enright et al. | |
| 2013/0299110 A1 | 11/2013 | Zhao et al. | |
| 2014/0044793 A1 | 2/2014 | Goll et al. | |

* cited by examiner

REVERSIBLE MICROCAPSULE FILTER CAKE

FIELD OF THE INVENTION

This invention relates to capsule manufacturing and more particularly to microcapsule cake products and processes of manufacturing a microcapsule filter cake.

DESCRIPTION OF THE RELATED ART

Various processes for microencapsulation, and exemplary methods and materials are set forth in Schwantes (U.S. Pat. No. 8,067,089), U.S. Pat. No. 6,592,990), Nagai et. al. (U.S. Pat. No. 4,708,924), Baker et. al. (U.S. Pat. No. 4,166,152), Wojciak (U.S. Pat. No. 4,093,556), Matsukawa et. al. (U.S. Pat. No. 3,965,033), Matsukawa (U.S. Pat. No. 3,660,304), Ozono (U.S. Pat. No. 4,588,639), Irgarashi et. al. (U.S. Pat. No. 4,610,927), Brown et. al. (U.S. Pat. No. 4,552,811), Scher (U.S. Pat. No. 4,285,720), Shioi et. al. (U.S. Pat. No. 4,601,863), Kirtani et. al. (U.S. Pat. No. 3,886,085), Jahns et. al. (U.S. Pat. Nos. 5,596,051 and 5,292,835), Matson (U.S. Pat. No. 3,516,941), Chao (U.S. Pat. No. 6,375,872), Foris et. al. (U.S. Pat. Nos. 4,001,140; 4,087,376; 4,089,802 and 4,100,103), Greene et. al. (U.S. Pat. Nos. 2,800,458; 2,800,457 and 2,730,456), Clark (U.S. Pat. No. 6,531,156), Saeki et. al. (U.S. Pat. Nos. 4,251,386 and 4,356,109), Hoshi et. al. (U.S. Pat. No. 4,221,710), Hayford (U.S. Pat. No. 4,444,699), Hasler et. al. (U.S. Pat. No. 5,105,823), Stevens (U.S. Pat. No. 4,197,346), Riecke (U.S. Pat. No. 4,622,267), Greiner et. al. (U.S. Pat. No. 4,547,429) and Tice et. al. (U.S. Pat. No. 5,407,609), among others and as taught by Herbig in the chapter entitled "Microencapsulation" in Kirk-Othmer Encyclopedia of Chemical Technology, V.16, pages 438-463.

More particularly, U.S. Pat. Nos. 2,730,456; 2,800,457; and 2,800,458 describe methods for capsule formation. Other useful methods for microcapsule manufacture are: U.S. Pat. Nos. 4,001,140; 4,081,376, 4,089,802, 4,105,823 and 4,444,699 describing a reaction between urea and formaldehyde; U.S. Pat. No. 4,100,103 describing reaction between melamine and formaldehyde; and British Pat. No. 2,062,570 describing a process for producing microcapsules having walls produced by polymerization of melamine and formaldehyde in the presence of a styrene-sulfonic acid. Alkyl acrylate-acrylic acid copolymer capsules are taught in U.S. Pat. No. 4,552,811. Each patent described throughout this application is incorporated herein by reference to the extent each provides guidance regarding microencapsulation processes and materials.

In interfacial polymerization a microcapsule wall from resins such as a polyamide, epoxy, polyurethane, polyurea or the like is formed at an interface between two phases. Riecke, U.S. Pat. No. 4,622,267, for example, discloses an interfacial polymerization technique for preparation of microcapsules. The core material is initially dissolved in a solvent and an aliphatic diisocyanate soluble in the solvent mixture is added. Subsequently, a nonsolvent for the aliphatic diisocyanate is added until the turbidity point is just barely reached. This organic phase is then emulsified in an aqueous solution, and a reactive amine is added to the aqueous phase. The amine diffuses to the interface, where it reacts with the diisocyanate to form polymeric polyurethane shells. A similar technique, used to encapsulate salts which are sparingly soluble in water in polyurethane shells, is disclosed in U.S. Pat. No. 4,547,429. U.S. Pat. No. 3,516,941 teaches polymerization reactions in which the materials to be encapsulated, or core material is dissolved in an organic, hydrophobic oil phase which is dispersed in an aqueous phase. The aqueous phase has dissolved materials forming aminoplast resin which upon polymerization form the wall of the microcapsule. A dispersion of fine oil droplets is prepared using high shear agitation. Addition of an acid catalyst initiates the polycondensation forming the aminoplast resin within the aqueous phase, resulting the formation of an aminoplast polymer which is insoluble in both phases. As the polymerization advances, the aminoplast polymer separates from the aqueous phase and deposits on the surface of the dispersed droplets of the oil phase to form a capsule wall at the interface of the two phases, thus encapsulating the core material. Urea-formaldehyde (UF), urea-resorcinol-formaldehyde (URF), urea-melamine-formaldehyde (UMF), and melamine-formaldehyde (MF), microcapsules can be formed by such processes.

Jahns, et. al., U.S. Pat. No. 5,292,835 teaches polymerizing esters of acrylic acid or methacrylic acid with polyfunctional monomers. Specifically illustrated are reactions of polyvinylpyrrolidone with acrylates such as butanediol diacrylate or methylmethacrylate together with a free radical initiator to form capsules surrounding an oil core.

Common microencapsulation processes can be viewed as a series of steps. First, the core material which is to be encapsulated typically an oil is emulsified or dispersed in a suitable dispersion medium. This medium is typically aqueous but involves the formation of a polymer rich phase. Most frequently, this medium is a solution of the intended capsule wall material. The solvent characteristics of the medium are changed such as to cause phase separation of the wall material. The wall material is thereby contained in a liquid phase which is also dispersed in the same medium as the intended capsule core material. The liquid wall material phase deposits itself as a continuous coating about the dispersed droplets of the emulsified oil.

The present invention is an improved method for dewatering microcapsules and microcapsule slurries. Dewatering a microcapsule slurry is advantageous for purposes of high solids concentration of material inputs into commercial processes. Dewatering enables achieving solid liquid separation enabling commercially advantageous and efficient transport of microcapsules for various industrial commercial processes.

Often, a microcapsule cake is desirable to be formed from a high solids content microcapsule slurry. With microcapsule slurries, typically when the volume-average microcapsule size is small, such as below about 15 um or in combination with some ultra fine microcapsules of less than 10 um, or ranging even from less than 0.01 to 5 um, the dewatering process can become very challenging. Normally, common techniques, such as use of filters and filter aid or microfiltration, might be utilized to attempt dewatering. However, filters plug, and adding filter aid often is ineffective and may contaminate the product. The alternative of microfiltration often is not economic and constrained by volume and solid content.

Another method for filtration involves adding flocculating agents. However, there is no report on how to control agglomeration in a manner such that the slurry can be easily filtered without affecting the intended target sized particles. A reversible agglomeration process and method of efficiently forming a reversible filter cake would be an advance in the art, and useful for many practical commercial applications.

DETAILED DESCRIPTION

Figure 1:
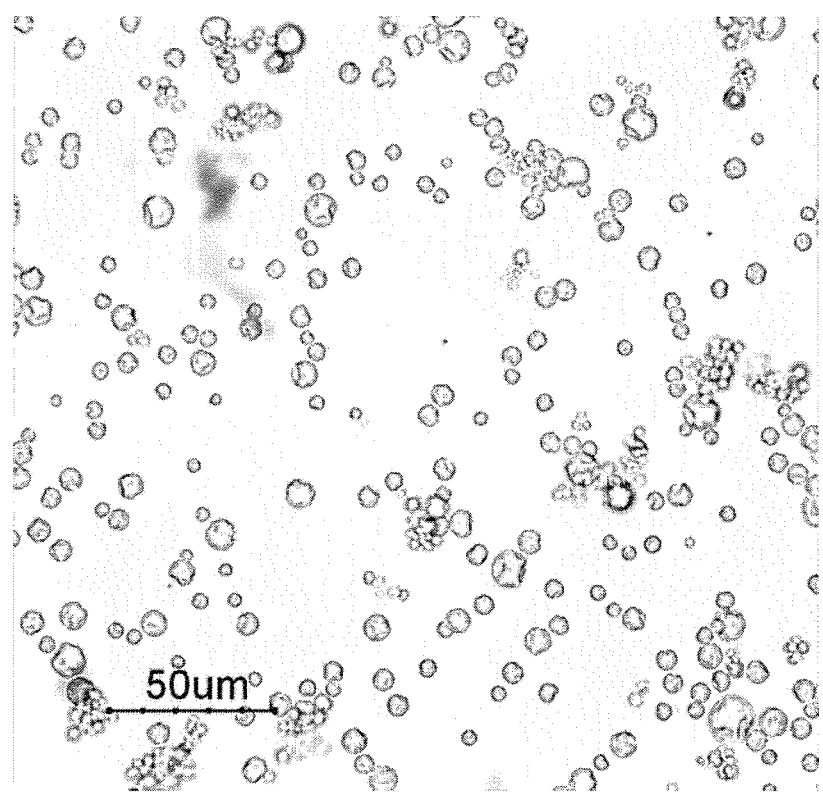
FIG. 1 is a microscopic image of a microcapsule slurry prepared according to Example 1.

The present invention teaches a controllable, reversible agglomeration method and a filter cake produced by such method.

The invention teaches a method of efficiently dewatering a microcapsule slurry to form a water re-suspendable filter cake of microcapsules. The process comprises providing an aqueous slurry of microcapsules dispersed in an aqueous solution; adding an agglomeration agent and dispersing the agglomeration agent into the aqueous slurry; adjusting the pH to a pH level sufficient to agglomerate the dispersed microcapsules; filtering the aqueous slurry of microcapsules by gravity, vacuum, centrifuging or pressure filtration to thereby form a filter cake of dewatered microcapsules. In one embodiment of the method, the microcapsules are cationic and the pH is adjusted to be alkaline, or at least a pH of 8. In a further embodiment, the pH is adjusted to a pH equal to or greater than 8 using a caustic material selected from sodium hydroxide, potassium hydroxide, ammonium hydroxide, a hydride of an alkali or alkaline earth metal, sodium hydride, potassium hydride, an alkoxide, a metal amide, or sodium amide.

In an alternative embodiment of the method of dewatering the microcapsule slurry, the microcapsules are cationic and the pH is adjusted to at least a pH of 5, or to at least a pH of 6, or even at least a pH of 8, or even a range of pH of from pH 4 to pH 9, or even a range of pH of from pH 4 to pH 10.

In the process of the invention, the agglomeration agent is selected from an alkali metal polyphosphate or an alkaline earth metal polyphosphate. The agglomeration agent can be sodium polyphosphate, sodium tetrapolyphosphate, sodium hexametaphosphate, and/or sodium tripolyphosphate.

In at least one embodiment of the process of the invention the microcapsules typically have a volume-average microcapsule size of 15 microns or less, and the microcapsules are cationic charged microcapsules, and in certain embodiments have an acrylate wall. Typically the solids content of the microcapsule slurry is desired to be increased. A filter cake can be formed by dewatering or filtering the microcapsule slurry. A slurry of microcapsules can be re-formed by resuspending the formed filter cake into an aqueous solution.

In a further embodiment the method of efficiently dewatering a microcapsule slurry to form a water re-suspendable filter cake of microcapsules comprises: providing an aqueous slurry of anionic microcapsules dispersed in an aqueous solution; adding an agglomeration agent; dispersing the agglomeration agent into the aqueous slurry; adjusting the pH to at least a pH of at least 6, or even to at least a pH of 8, or even a range of pH of from pH 4 to pH10 or greater; and filtering the aqueous slurry of microcapsules by gravity, vacuum or pressure filtration to form a filter cake of dewatered microcapsules.

Compared to prior art processes, the process of the invention provides a straightforward and efficient method to prepare microcapsule filter cake, particularly of microcapsule with average volume size below 15 um. The technique is functional across a wide pH range and the filter cake made is reversible, in that the cake can be redispersed.

The microcapsules useful in the process of the invention can be made by any of the various art processes for microencapsulates, including the processes described herein in the Description of Related Art section. The dewatering method is widely applicable and is particularly effective with polyacrylate microcapsules but not limited to such. The process of the invention is particularly useful with cationic microcapsules.

The agglomeration agent useful in the invention to form a filter cake of dewatered microcapsules is an alkali metal polyphosphate or an alkaline earth metal polyphosphate. Examples of such agglomeration agent include soldium-polyphosphate, sodium tetrapolyphosphate, sodium hexametaphosphate and sodium tripolyphosphate. These materials are particularly suited for use with cationic or nonionic microcapsules, or microcapsules with such coatings.

With anionic microcapsules or anionic coated microcapsules preference is for an agglomeration agent selected from an alkaline earth metal salt such as magnesium chloride, calcium chloride or barium chloride, or even aluminum salt such as aluminum chloride.

The agglomeration agent is typically used at less than 15%, less than 10%, less than 8%, or even less than 5% by weight, based on weight of the microcapsule slurry. The agglomeration agent can be used in an amount from 0.5 to 10% by weight, from 1 to 8% by weight, or even from 0.25% to 5% by weight based on weight of the microcapsule slurry.

The microcapsule slurry can optionally be combined with other materials provided they do not substantially interfere with the effectiveness of the agglomeration agent. The optional materials can include any of various surfactant can be added, selected to have less charge than the cationic microcapsules. Other optional materials can include materials that influence properties of the microcapsule wall material of the microcapsules. Such materials can change rheology, influence permeability, rate of disintegration, or porosity of the wall. Such optional materials may include sucrose octyl stearate, polysaccharides, polyethylene glycol, esters of polyethylene glycol, esterified polyol, or saccharide esters. Advantageously, a certain portion of such optional materials are carried with and incorporated in the microcapsule wall surrounding the capsule core.

Also useful in the process of the invention are microcapsules which are further coated with a second coating such as a cationic coating as taught in Popplewell et. al, U.S. Pub. No. 2005/0112152.

The core material of the microcapsules can comprise any of various core materials include dyes, chromogens, fragrances, phase change materials, solvents, actives such as biological actives, agricultural materials and actives, nutrients, pharmaceuticals, benefit agents, such as perfumes, silicones, waxes, flavors, vitamins, fabric softening agents, well site lubricants, cement casing hardeners, adhesives, hardeners, curatives and the like.

Optionally, the microcapsules can be coated with various second coatings, such as cationic coatings or coating with polymers such as taught in Smets et. al. U.S. Pat. No. 8,759,275. Such coated microcapsules with encapsulated benefit agents have a high and even deposition profile across multiple different surfaces. Such encapsulated benefit agents and specific classes of amine containing polymers when combined, provide a high and even deposition profile to the microcapsules across multiple different surfaces. The process of the invention can facilitate dewatering of such coated microcapsules.

In one aspect the optional coating on the microcapsules can comprise one or more polymers selected from the group consisting of polyvinyl amines, polyvinyl formamides, and polyallyl amines and copolymers thereof. Coating can optionally or further include cationic polymers include poly vinyl polymers, having the monomer generic formula —C(R2)(R1)-CR2R3-. Where R1 is any alkanes from C1-C25 or H; the number of double bonds ranges from 0-5. Furthermore, R1 can be any alkoxylated fatty alcohol with any alkoxy carbon-length, number of alkoxy groups and C1-C25 alkyl chain length.

In the above formula, R2 can be H or CH3; and R3 can be —Cl, —NH2 (i.e., poly vinyl amine and its copolymers and N-vinyl formamide, known a Lupamin 9095 from BASF Corporation), —NHR1, —NR1R2, —NR1R2 (where R6=R1, R2, or —CH2-COOH or its salt), —NH—C(O)—H, —C(O)—NH2 (amide), —C(O)—N(R2)(R2')(R2"), —OH, styrene sulfonate, pyridine, pyridine-N-oxide, quaternized pyridine, imidazolinium halide, imidazolium halide, imidazole piperdine, pyrrolidone, alkyl-substituted pyrrolidone, caprolactam or pyridine, phenyl-R4 or naphthalene-R5 where R4 and R5 are R1, R2, R3, sulfonic acid or its alkali salt —COOH, —COO-alkali salt, ethoxy sulphate or any other organic counter ion. Any mixture of these R3 groups may be used. Further suitable cationic polymers containing hydroxy alkyl vinyl amine units, are disclosed in U.S. Pat. No. 6,057,404.

Unless otherwise indicated, all measurements herein are on the basis of weight and in the metric system. All references cited herein are expressly incorporated herein by reference.

Example 1

Figure 2:
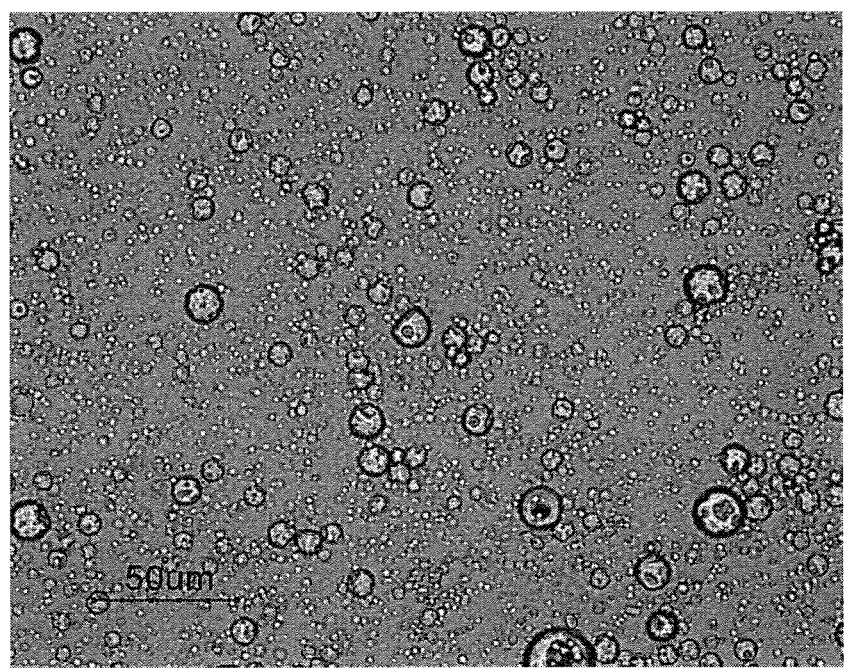
FIG. 2 is a microscopic image of a redispersed slurry, of Example 1, redispersed from filter cake.

To a cationic charged microcapsule slurry prepared by the process of U.S. Pat. No. 8,067,089 (100 g, solids: 41%, volume median size: (8 um) was added 2.0 g of sodium polyphosphate. Until all the sodium polyphosphate dissolved, sodium hydroxide (20%) was added dropwise with mixing to adjust the pH value to 8. The resulting slurry was sticky, but the sticky slurry was able to be easily filtered by vacuum or pressure filtration while the non-treated slurry is not able to be filtered. FIG. 1 is a microscope image of the agglomerated slurry. FIG. 2 is a microscope image of the redispersed slurry from the filter cake. From FIG. 1 it can be seen that the fine microcapsules were agglomerated, but the larger ones remained integrated. FIG. 2 shows an absence of agglomerations when the cake was reslurried.

Example 2

To an anionic charged microcapsule slurry prepared by the process of U.S. Pat. No. 8,551,935 (100 g, solids: 40%, volume median size: (10 um) was added 3.0 g of magnesium chloride Solution (33%). The processes of Examples 1 through 4 can be employed. Sodium hydroxide (20%) was added dropwise with mixing to adjust the pH value to 7. The slurry was sticky but can be easily filtered by vacuum or pressure filtration while a comparable non-treated slurry is not able to be filtered.

The process of the invention is an efficient method for dewatering a microcapsule slurry. The process of the invention results in a filter cake which is reversible. The filter cake produced according to the process of the invention is able to be redispersed from the filter cake into an aqueous solution forming an aqueous slurry.

All documents cited in the specification herein are, in relevant part, incorporated herein by reference for all jurisdictions in which such incorporation is permitted. The citation of any publication is for its disclosure prior to the filing date and should not be construed as an admission that such publication is prior art or that the present invention is not entitled to antedate such publication by virtue of prior invention. To the extent that any meaning or definition of a term in this document conflicts with any meaning or definition of the same term in a document incorporated by reference, the meaning or definition assigned to that term in this document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. No unclaimed language should be deemed to limit the invention in scope. Any statements or suggestions herein that certain features constitute a component of the claimed invention are not intended to be limiting unless reflected in the appended claims.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of dewatering a microcapsule slurry to form a water re-suspendable filter cake of microcapsules comprising:
   providing an aqueous slurry of microcapsules dispersed in an aqueous solution, wherein the microcapsules are cationic microcapsules having an acrylate wall;
   adding an agglomeration agent selected from an alkali metal polyphosphate or an alkaline earth metal polyphosphate and dispersing the agglomeration agent into the aqueous slurry of microcapsules;
   adjusting the pH of the aqueous slurry of microcapsules to at least a pH of 5 to agglomerate the microcapsules;
   centrifuging or filtering the aqueous slurry of microcapsules by gravity, vacuum, or pressure filtration to form a filter cake of dewatered microcapsules.

2. The method according to claim 1 wherein the pH is adjusted using a caustic material selected from sodium hydroxide, potassium hydroxide, ammonium hydroxide, a hydride of an alkali or alkaline earth metal, an alkoxide, or a metal amide.

3. The method according to claim 1, wherein the agglomeration agent is sodium polyphosphate.

4. The method according to claim 1 wherein the agglomeration agent is selected from the group consisting of sodium tetraphosphate, sodium hexametaphosphate and sodium tripolyphosphate.

5. The method according to claim 1 wherein the microcapsules have a volume-average microcapsule size of 15 microns or less.

6. The method according to claim 1 wherein the microcapsules of the aqueous slurry of microcapsules are coated with cationic polymer selected from the group consisting of polyvinyl amine, polyvinyl formamide, polyallyl amine and copolymers of any of the foregoing.

7. A method of dewatering a microcapsule slurry to form a water-resuspendable filter cake of microcapsules comprising:
providing an aqueous slurry of microcapsules dispersed in an aqueous solution wherein the microcapsules are cationic microcapsules having an acrylate wall, adding an agglomeration agent selected from an alkali metal polyphosphate or an alkaline earth metal polyphosphate to the aqueous slurry of microcapsules and
dispersing the agglomeration agent into the aqueous slurry of microcapsules; adjusting the pH of the aqueous slurry of microcapsules from pH 4 to 10 to agglomerate the microcapsules; and centrifuging or filtering the aqueous slurry of microcapsules by gravity, vacuum, or pressure filtration to form a filter cake of dewatered microcapsules.

8. The method according to claim 7 wherein the pH is adjusted using a caustic material selected from sodium hydroxide, potassium hydroxide, ammonium hydroxide, a hydride of an alkali or alkaline earth metal, an alkoxide or a metal amide.

9. The method according to claim 7 wherein the microcapsules have a volume-average microcapsule size of 15 microns or less.

10. The method according to claim 7 wherein the microcapsules of the aqueous slurry of microcapsules are coated with cationic polymer selected from the group consisting of polyvinyl amine, polyvinyl formamide, poly allyl amine and copolymers of any of the foregoing.

* * * * *